United States Patent [19]

Kientzler

[11] Patent Number: Plant 7,371

[45] Date of Patent: Oct. 30, 1990

[54] IMPATIENS PLANT NAMED PATULA

[75] Inventor: Ludwig Kientzler, Gensingen, Fed. Rep. of Germany

[73] Assignee: Paul Ecke Ranch, Encinitas, Calif.

[21] Appl. No.: 394,747

[22] Filed: Aug. 16, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A new and distinct cultivar of Impatiens plant named Patula characterized by its bright orange-red flowers which are light pink at the outer edges; early, continuous and prolific flowering, dark reddish-green foliage, and its upright and vigorous growth habit with good self-branching.

1 Drawing Sheet

The present invention relates to a new and distinctive cultivar of Impatiens plant, botanically known as Impatiens, and known by the cultivar name Patula. The new cultivar was developed by me in Gensingen, Federal Republic of Germany through controlled breeding by crossing male and female parents which are unknown at this time.

Asexual reproduction by terminal cuttings taken at Gensingen, Federal Republic of Germany, has shown that the unique features of this new Impatiens are stabilized and are reproduced true to type in successive propagations.

The following characteristics distinguish the new Impatiens from both its parent varieties and other cultivated Impatiens of this type known and used in the floriculture industry.

(1) Orange-red and light pink bicolored flowers.

(2) Early and prolific flowering, with the flowers being long-lasting and flowering continuous.

(3) Dark reddish-green foliage.

(4) Upright and vigorous growth habit, with very good self-branching.

The accompanying colored photograph is a top perspective view of the new cultivar, showing color as true as it is reasonably possible to obtain in a colored reproduction of this type.

The following is a detailed description of my new Impatiens cultivar based on plants produced under commercial practice in Encinitas, Calif. The described characteristics were noted between December 10–20 and were based on unrooted cuttings rooted under intermittent mist and then transplanted into 6" pots, with flowering commencing in November. Color references are made to The Royal Horticultural Society Colour Chart (RHS), except where general terms of ordinary dictionary significance are used.

Parentage:

A. *Type cutting.*—Tip, with stems 2–3 cm long developing to 4–5 cm after 21 days following propagation.

B. *Time to initiate roots.*—8–10 days at 23° C.; nicely developed root mass in 18–21 days.

C. *Rooting habit.*—Numerous, fibrous adventitious roots from the stem.

Plant description:

A. *Form.*—Symmetrical, bush shaped, flowering herb, with self-branching characteristics giving the plant a full appearance.

B. *Habit of growth.*—Vigorous, self-branching, medium habit, producing whorls of leaves and flowers on branched stems. Growth is indeterminate and flowering is continuous.

C. *Foliage description.*—Leaves are simple. Lower leaves on stem are opposite. Higher leaves in whorls of mostly 3. (1) Leaf shape: Mostly ovate, tip acuminate to acute, base acute. (2) Leaf blade size: 7–9 cm long×3.5–4.5 cm wide. (3) Leaf margin: Ciliated and lightly serrated. (4) Leaf texture: (a) Upper surface: Glabrous. (b) Under surface: Glabrous. (5) Leaf color: Dark green, with reddish veins and mid-vein. (a) Upper surface: Darker than 147A. (b) Under surface: Near 183A. (6) Venation: pinnate.

Flowering description:

(A) *Flowering habit.*—Very floriferous, flowering continuous. Flowers develop progressively around the whorl of leaves, taking 5–7 days from buds which show color, to bloom. Flowers are single and large, lasting for 2–3 weeks.

(B) *Natural flowering season.*—Flowering is indeterminate and occurs throughout the year. Quantity of flowers increases with increasing light intensity and duration.

(C) *Flower buds.*—Ellipsoidal and covered with 5 sepals. A reddish-green approximately 5 cm long spur originates from the base of the major sepal. Two additional, rudimentary sepals are fused to back of the top petal and a sepal on either side of the pedicel.

(D) *Flowers borne.*—Singly, on pedicels 4.5 cm long; pedicels greenish in color.

(E) *Quantity of flowers.*—Floriferous. One or two flowers per leaf occurring progressively around the whorl of leaves so that tight buds to mature blooms are visible at the same time in large numbers.

(F) *Petals.*—(1) Number of petals: Five (5). (2) Shape: Two petal heart shaped with wide base, all other petals heart shaped with pointed base. All petals overlap. (3) Color: Intense orange-red at the basal end of the petals, fading to a light pink at the outer edge. (a) Upper surface: Orange-red, brighter than 33A; pink, near 56B at edges. (b) Under surface: Near 33B. (4) Size of flowers: 4.5 cm across.

(G) *Reproductive organs.*—(1) Stamens: Five (5) with the lower stamen being shorter than the other stamens. Stamens are united in an asymmetrical tube surrounding the ovary. (2) Anthers: Hooded, cream fused with red. (3) Pollen: Cream color. (4) Stigma: Five pointed star, colorless. (5) Styles: Very short, reddish in color. (6) Ovary: 5 celled, 4–5 mm. long until fertilized, purple in color.

I claim:

1. A new and distinct cultivar of Impatiens plant named Patula, as illustrated and described.

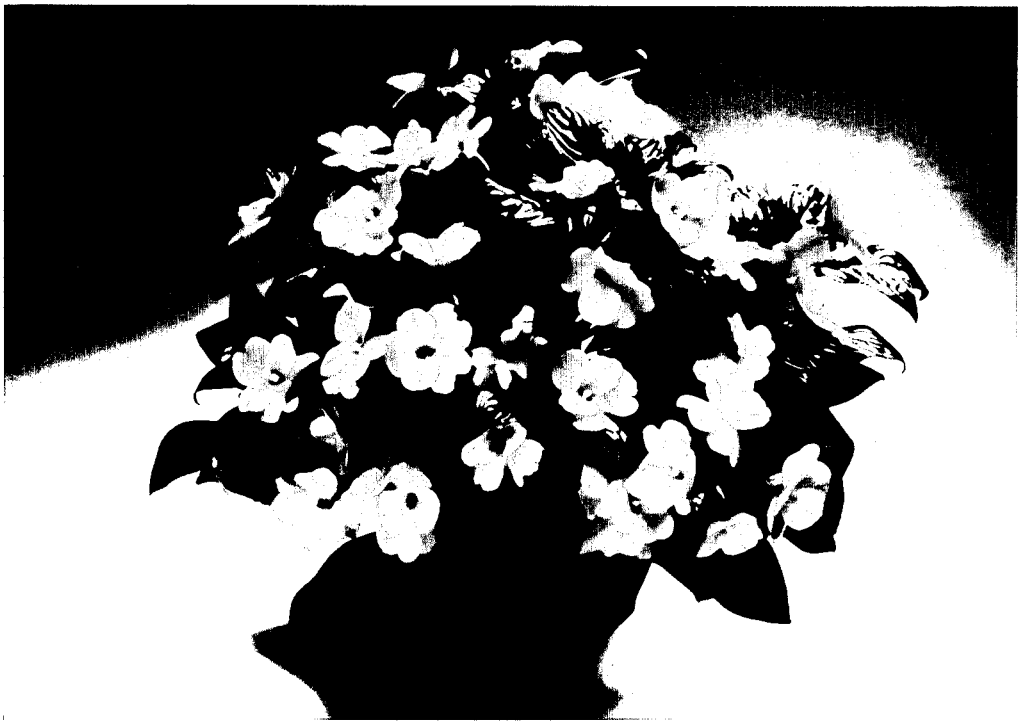

* * * * *